United States Patent
Dong et al.

[11] Patent Number: 5,830,501
[45] Date of Patent: Nov. 3, 1998

[54] DOSAGE FORM COMPRISING HYDROPHILIC POLYMER

[75] Inventors: Liang C. Dong, Mountain View; Michael H. Dealey, San Francisco; Terry L. Burkoth; Patrick S. -L. Wong, both of Palo Alto; Jerry D. Childers; Brian L. Barclay, both of Sunnyvale, all of Calif.

[73] Assignee: ALZA Corporation, Palo Alto, Calif.

[21] Appl. No.: 964,548

[22] Filed: Oct. 21, 1992

Related U.S. Application Data

[62] Division of Ser. No. 804,137, Dec. 6, 1991, Pat. No. 5,200,195, and Ser. No. 963,962, Oct. 21, 1992, Pat. No. 5,348,746, and Ser. No. 964,538, Oct. 21, 1992, Pat. No. 5,348,746, and Ser. No. 963,967, Oct. 21, 1992, and Ser. No. 964,162, Oct. 21, 1992, Pat. No. 5,266,332, and Ser. No. 964,603, Oct. 21, 1992.

[51] Int. Cl.⁶ .................................................. A61K 9/24
[52] U.S. Cl. ........................................... 424/473; 424/472
[58] Field of Search ..................................... 424/473, 472

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,111,201 | 9/1978 | Theeuwes | 128/260 |
| 4,111,202 | 9/1978 | Theeuwes | 128/260 |
| 4,111,203 | 9/1978 | Theeuwes | 128/260 |
| 4,160,020 | 7/1979 | Ayer et al. | 424/15 |
| 4,186,184 | 1/1980 | Zaffaroni | 424/14 |
| 4,200,098 | 4/1980 | Ayer et al. | 128/260 |
| 4,203,439 | 5/1980 | Theeuwes et al. | 128/260 |
| 4,309,996 | 1/1982 | Theeuwes | 128/260 |
| 4,327,725 | 5/1982 | Cortese et al. | 128/260 |
| 4,449,983 | 5/1984 | Cortese et al. | 604/892 |
| 4,612,008 | 9/1986 | Wong et al. | 604/892 |
| 4,800,056 | 1/1989 | Eckenhoff et al. | 264/129 |
| 4,837,111 | 6/1989 | Deters et al. | 424/473 |
| 4,940,465 | 7/1990 | Theeuwes et al. | 604/892.1 |
| 4,971,790 | 11/1990 | Magruder et al. | 424/78 |
| 5,019,396 | 5/1991 | Ayer et al. | 424/473 |
| 5,021,053 | 6/1991 | Barclay et al. | 604/892.1 |
| 5,057,321 | 10/1991 | Edgren et al. | 424/413 |

*Primary Examiner*—D. Gabrielle Brouiellette
*Attorney, Agent, or Firm*—Paul L. Sabatine; Christopher P. Rogers

[57] ABSTRACT

A dosage form is disclosed comprising means for lessening the tackiness and/or irritation of the components of the dosage form to mucosal tissue. The dosage form provides means for forming in the dosage form a floc comprising a drug, which floc, when delivered from the dosage form, lessens the tackiness and/or irritation of the mucosal tissue of a warm-blooded recipient.

1 Claim, 7 Drawing Sheets

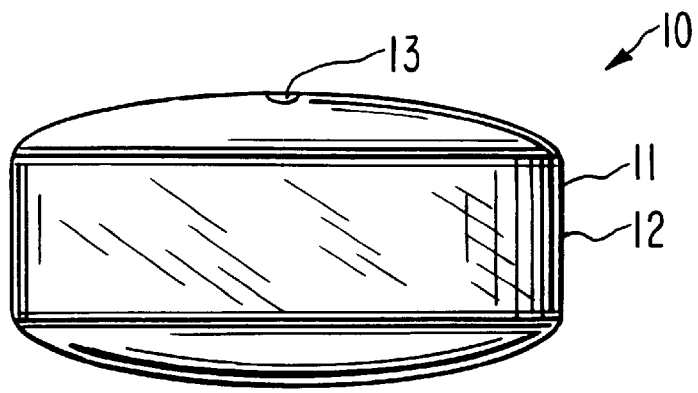
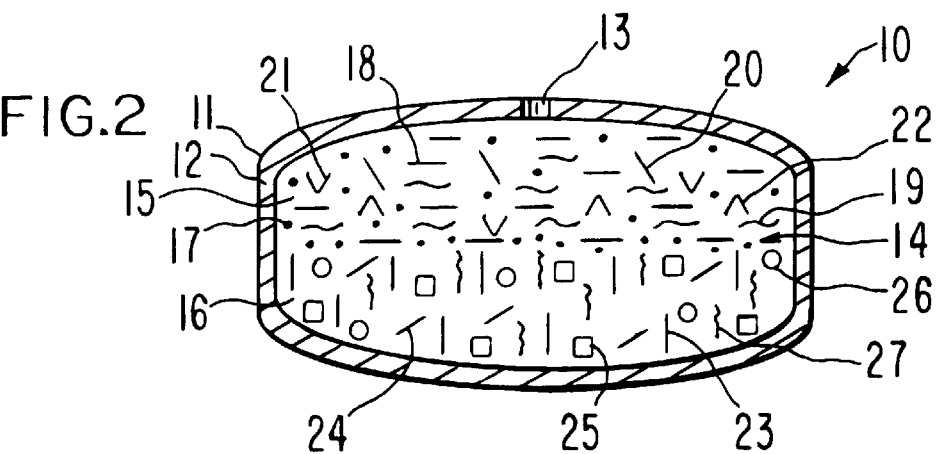
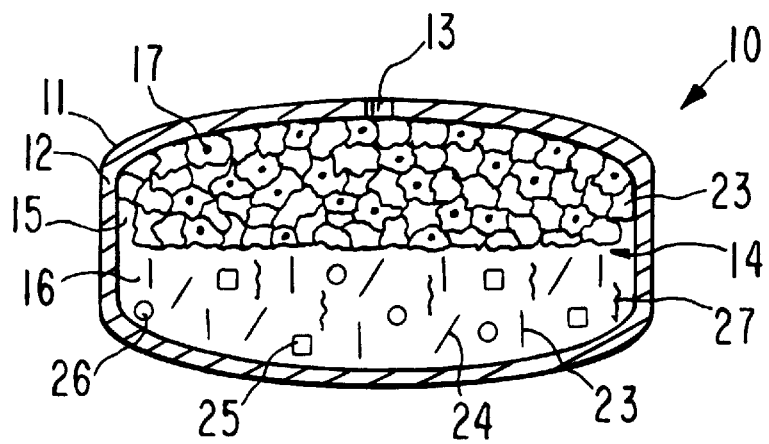

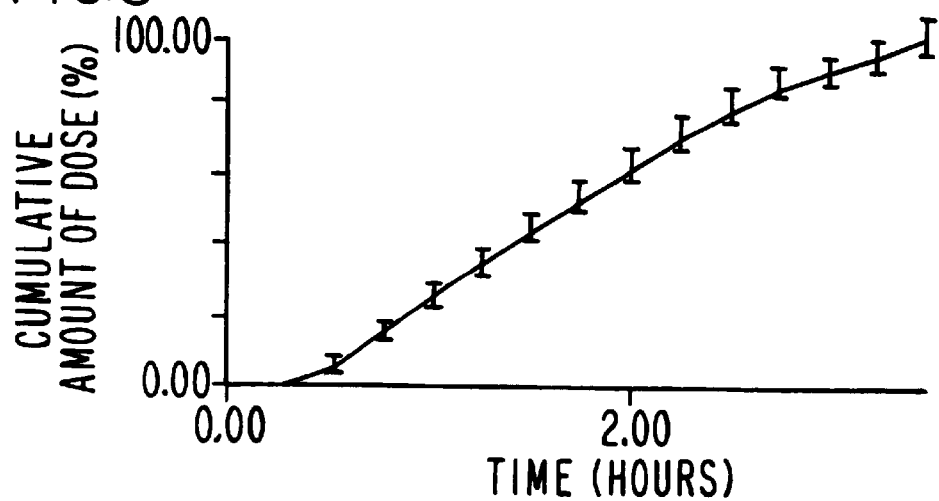
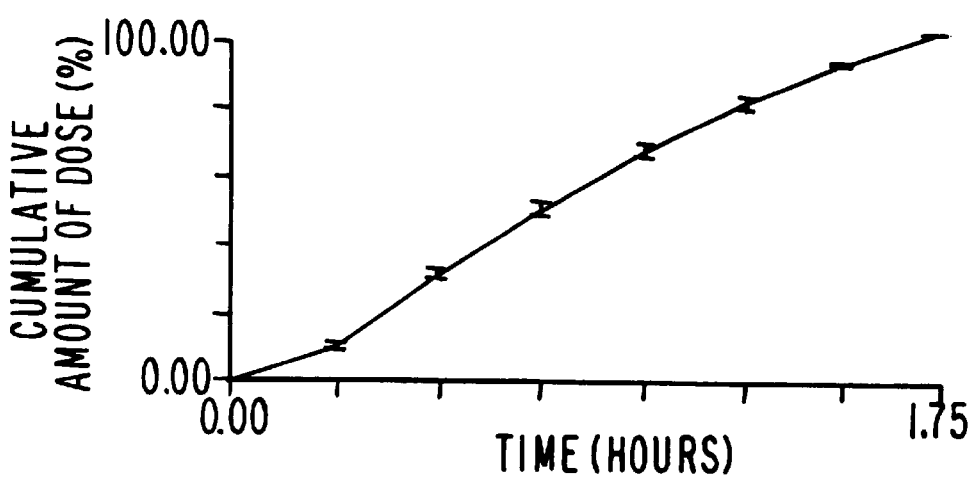
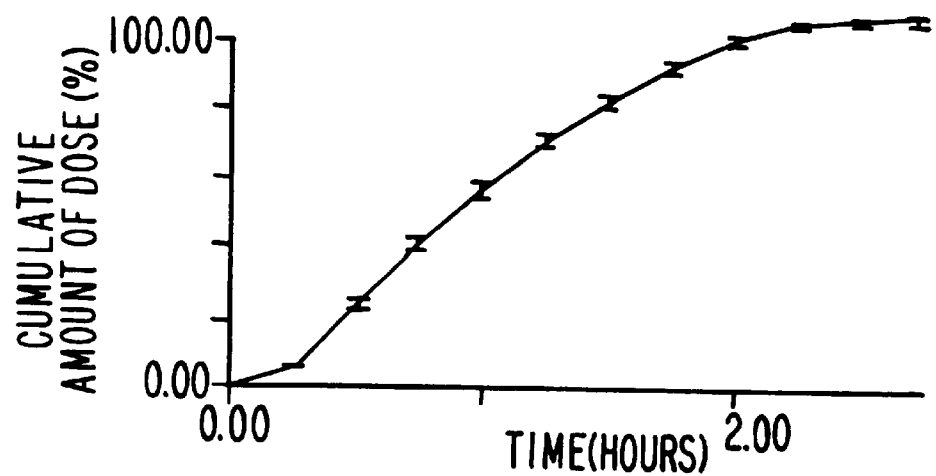

DOSAGE FORM COMPRISING HYDROPHILIC POLYMER

CROSS-REFERENCE TO RELATED APPLICATIONS

This application is a division of Ser. No. 07/804,137 filed Dec. 6, 1991, now U.S. Pat. No. 5,200,195 issued Apr. 6, 1993, which application is incorporated herein by reference and benefit is claimed of its filing date. This application is copending with applicants' U.S. applications, identified by attorney's docket numbers ARC 1955 Div. 1, ARC 1955 Div. 2, ARC 1955 Div. 3, ARC 1955 Div. 4 and ARC 1955 Div. 6 now U.S. Ser. No. 07/963,962; now U.S. Pat. No. 5,254,349; U.S. Ser. No. 07/964,538; now U.S. Pat. No. 5,348,746 U.S. Ser. No. 07/963,967 pending; U.S. Ser. No. 07/964,162 now U.S. Pat. No. 5,266,332; and U.S. Ser. No. 07/964,603 pending all filed Oct. 21, 1992 respectively. These applications are assigned to the ALZA Corporation of Palo Alto, Calif.

FIELD OF THE INVENTION

This invention pertains to both a novel and unobvious osmotic delivery system. More particularly, the invention relates to an osmotic system comprising a drug dispersed in a polymer floc, wherein the floc comprises a hydrophilic polymer flocculated above its lower critical solution temperature to provide a floc with the drug dispersed therein. The invention concerns further a method comprising administering a drug essentially-free of mucosal tackiness, and also a process comprising the in situ flocculation of a polymer above its lower critical solution temperature to provide a flocculate comprising the drug.

BACKGROUND OF THE INVENTION

Osmotic delivery systems for administering a beneficial drug to a biological, fluid environment of use are known to the prior medical and veterinary arts. For example, in U.S. Pat. No. 3,845,770 issued to Theeuwes and Higuchi, and in U.S. Pat. No. 3,916,899 issued to the same patentees, a novel device is disclosed comprising a wall that surrounds a compartment comprising a beneficial agent. The wall is permeable to the passage of fluid, and it comprises a passageway that is preformed during manufacture of the device, or is formed during its use through the wall for delivering the beneficial drug from the device. The devices disclosed in these patents release the beneficial drug by fluid being imbibed through the wall into the compartment at a rate determined by the permeability of the wall and the osmotic pressure gradient across the wall. The fluid imbibed into the device mixes with the beneficial drug to form an aqueous solution comprising the drug that is dispensed through the passageway from the device at a controlled rate over time. The devices of these patents are extraordinarily effective for delivering a beneficial drug that is stable and soluble in aqueous and biological fluids and exhibits an osmotic pressure gradient across the wall against the fluid. The devices are effective also for delivering a beneficial drug that is mixed with an osmotically effective solute soluble in fluid and exhibits an osmotic pressure gradient across the wall against an external, aqueous fluid.

A pioneering improvement in osmotic devices was presented to the pharmaceutical dispensing art by inventor Theeuwes in U.S. Pat. Nos. 4,111,202; 4,111,203; and 4,203,439. In these patents, the delivery kinetics of the devices were enhanced for delivering therapeutic drugs possessing differing degrees of solubility in aqueous fluids. The kinetics were improved for these devices, by manufacturing the devices with a drug compartment separated by a flexible film from a push compartment. The devices deliver the beneficial drug by fluid being imbibed through the wall into the push compartment to fill the compartment with fluid that acts as a driving force and causes the film to move. The film moves against the beneficial drug compartment and the driving force thereby pushes the beneficial agent through a passageway from the device.

A quantum advancement in osmotic delivery devices was made by Cortese and Theeuwes in U.S. Pat. No. 4,327,725 and by Wong, Barclay, Deters and Theeuwes in U.S. Pat. No. 4,612,008. The devices disclosed in these patents comprise a semipermeable wall that surrounds a compartment. The compartment comprises a beneficial drug formulation and a hydrogel. These devices operate by imbibing fluid into the compartment, wherein it contacts the biologically active drug formulation and forms a dispensable aqueous formulation, and wherein it contacts the hydrogel causing it to expand and push the dispensable aqueous formulation through a passageway from the device.

The delivery devices disclosed in the above patents operate successfully for their intended use, and the devices can deliver many beneficial drugs for their intended therapy. While these devices represent an advancement in the art, their use often is limited in therapy. For instance, presently delivery devices do not lend themselves for the fast delivery of a drug over a short period of time, because devices made with a thin wall, needed for such fast drug delivery, are subjected to cracks and wall ruptures attributed to high osmotic and hydrodynamic pressures generated within the device. Also, in some instances, devices comprising a viscous, sticky polymer used for transporting a drug from the device to a mucosal tissue, can lead to unwanted effects such as the device sticking to mucosal tissue that may cause mucosal irritation or ulceration of the mucosal tissue.

It will be appreciated by those versed in the dispensing arts, that if a delivery system is provided for administering a drug at a fast controlled rate over a short period of time, such a delivery system would have a positive value and represent an advancement in the dispensing arts. Likewise, it will be self-evident to those versed in the dispensing arts, that a pressing need exists for a delivery system that is essentially-free of stickiness and essentially-free of mucosal irritation and mucosal ulceration, and that if such a delivery system is provided, the delivery system would have a practical application in the field of human and veterinary medicine.

OBJECTS OF THE INVENTION

Accordingly, in view of the above presentation, it is an immediate object of this invention to provide an improved osmotic system for the controlled and continuous delivery of a beneficial drug that overcomes the shortcomings associate with the prior art known osmotic systems.

Another object of the invention is to provide an osmotic system that is a self-contained, self-starting, and self-powered osmotic system, that is easy to manufacture, and can be used for dispensing a beneficial drug to a human mucosal environment for a needed therapy.

Another object of the invention is to provide a novel osmotic dosage form adapted for a patient's convenience that enables patient compliance for executing a prescribed therapeutic program.

Another object of the invention is to provide an osmotic system for administering a drug accompanied by a lessening of the drug's mucosal tissue irritation.

Another object of the present invention is to provide an osmotic drug delivery system for the administration of a drug comprising means for lessening the mucosal stickiness of the drug for correspondingly decreasing the drug's ability to produce tissue injury, while concomitantly administering the drug in a therapeutically effective dosage amount.

Another object of the present invention is to provide an osmotic drug delivery system for the administration of a drug comprising means for lessening the mucosal stickiness of a polymer as a dispersant for correspondingly decreasing the polymer's ability to produce tissue injury, which concomitantly administering the drug in a therapeutically effective dosage amount.

Another object of the invention is to provide an osmotic system comprising an essentially mucosa adhesiveless drug formulation useful for administering a hydrophobic drug to a drug-receptor mucosal tissue.

Another object of the invention is to provide an osmotic system comprising means for lessening the hydrostatic pressure generated in the system during its operation for correspondingly maintaining the physical structure and operating integrity of the osmotic system.

Another object of the invention is to provide an osmotic system manufactured as an osmotic dosage form for the controlled delivery of a beneficial drug to the oral cavity comprising the buccal and sublingual cavities of an animal, and particularly in a human.

Another object of the invention is to provide an oral osmotic dosage form useful for delivering a drug into the mouth of a patient, which drug is difficult to deliver and now can be delivered by the subject dosage form at a pharmaceutically effective rate over a known period of time.

Another object of the invention is to provide an osmotic dosage form comprising a drug and a polymer, which polymer above its lower critical solution temperature precipitates in imbibed fluid with the drug dispersed in the precipitate that can administer a potentially irritating drug into the mouth of a human without causing irritation to the buccal membranes.

Another object of the invention is to provide an orally administrable osmotic dosage form comprising a compartment, wherein the compartment comprises (1) a first composition comprising a drug that can be from insoluble to very soluble in an aqueous fluid and a polymeric carrier therefore, and (2) a second composition comprising an expandable driving composition comprising a hydrophilic polymer that expands to diminish the space occupied by the first composition, thereby delivering the first composition from the dosage form, and wherein the dosage form is characterized by the polymer in the first composition exhibiting a lower critical solution temperature that flocculates in solution to form a floc with the drug dispersed in the floc to provide an essentially-free mucosa adhesiveless drug formulation that is substantially free of sticking to any area in the mouth or in the gastrointestinal tract.

Another object of the invention is to provide an osmotic dosage form comprising a first, dispensable composition that comprises a drug, a hydrophilic polymer, and a dehydrating compound, which compound depresses the lower critical solution temperature of the polymer by dehydrating the polymer in solution with the drug dispersed in the resulting depressed polymer for providing a dispensable drug-polymer composition.

Another object of the invention is to provide a dosage form comprising an anti-fungal drug, such as nystatin, wherein the dosage form comprises a flavoring agent or more than one flavoring agent for taste, masking the bitter taste of the anti-fungal drug, such as nystatin.

Other objects, features, aspects and advantages of this invention will be more apparent to those versed in the art from the following detailed specification taken in conjunction with the accompanying drawing figures and the accompanied claims.

BRIEF DESCRIPTION OF DRAWINGS

In the drawing figures, which are not drawing to scale, but are set forth to illustrate various embodiments of the invention, the drawing figures are as follows:

Drawing FIG. 1 is a view of an osmotic system manufactured by the invention as a dosage form for administering a beneficial drug to a biological environment of use;

Drawing FIG. 2 is an opened view of the osmotic system of drawing FIG. 1 for illustrating the structure and the internal components of the osmotic system;

Drawing FIG. 3 is an opened view of the osmotic system of drawing FIGS. 1 and 2 depicting a wall that surrounds an internal compartment with the osmotic system in an operating mode and exhibiting a flocculated hydrophilic polymer above its lower critical solution temperature in the compartment;

Drawing

Drawing

Drawing

Drawing FIGS. 8 through 15 depict the cumulative amount of a drug released over time for a multiplicity of osmotic systems provided by the invention.

In the drawings and specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWING FIGURES

Figure 4:
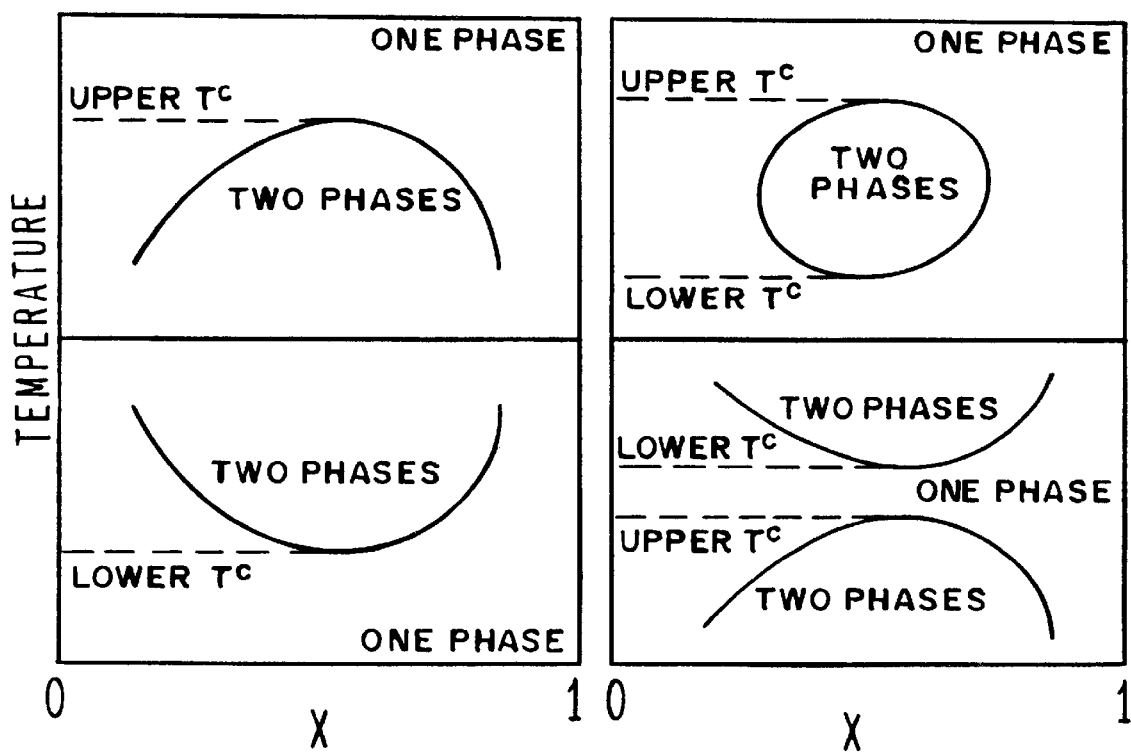
FIG. 4 depicts phase diagrams comprising phase stability in four binary liquid mixtures.

Turning now to the drawing figures in details, which are examples of various osmotic delivery systems provided by this invention, and which examples are not to be considered as limiting one example of an osmotic delivery system manufactured as a dosage form is indicated in drawing FIG. 1 by the numeral 10. In drawing FIG. 1, dosage form 10 is seen comprised of a body 11, comprising a wall 12 that surrounds and enclosed an internal compartment, not seen in drawing FIG. 1. Dosage form 10 comprises at least one exit means 13 in wall 12 which exit means 13 connects the exterior environment of use with the interior of dosage form 10.

In drawing FIG. 2, dosage form 10 of drawing FIG. 1 is seen in opened view. In drawing FIG. 2, dosage form 10 comprises body 11, wall 12, which wall 12 surrounds and defines an internal compartment 14. Wall 12 comprises at least one exit means 13 that connects compartment 14 with the exterior of dosage form 10. Wall 12 of dosage form 10 can comprises more than one exit means, as presented later in the specification.

Wall 12 of dosage form 10 comprises totally, or in at least a part, a semipermeable composition that is permeable to the passage of an exterior fluid present in the environment of use. Wall 12 is substantially impermeable to the passage of a drug and to other optional ingredients that may be present in compartment 14. The semipermeable wall 12 is substantially inert, that is, wall 12 maintains its physical and chemical integrity during the dispensing of a drug from dosage form 10. Wall 12, in a presently preferred embodiment, comprises totally, or in at least a part, a member selected from the group consisting of a cellulose ether, a cellulose ester, and a cellulose ester-ether. The cellulosic polymer has a degree of substitution, D.S., on the anhydroglucose unit, from greater than 0 up to 3 inclusive. By degree of substitution is meant the average number of hydroxyl groups originally present on the anhydroglucose unit comprising the cellulose polymers that are replaced by a substituting group. Representative polymers for providing wall 12 comprise a member selected from the group consisting of cellulose acylate, cellulose diacylate, cellulose triacylate, cellulose acetate, cellulose diacetate, cellulose triacetate, mono-, di-, and tricellulose alkanylates, mono-, di- and tricellulose aroylates, and the like. Exemplary polymers include cellulose acetate having a D.S. up to 1 and an acetyl content up to 21%; cellulose acetate having an acetyl content of 32 to 39.8%; cellulose acetate having a D.S. of 1 to 2 and an acetyl content of 21 to 35%; cellulose acetate having a D.S. of 2 to 3 and an acetyl content of 33 to 44.8%; and the like. More specific cellulose polymers comprise cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl of 2 to 29%, a butyryl content of 17 to 53%, and a hydroxyl content of 0.5 to 4.7%; cellulose triacylates having a D.S. of 2.9 to 3 such as cellulose triacetate, cellulose trivalerate, cellulose trilaurate, cellulose tripalmitate, cellulose trisuccinate, and cellulose trioctanoate; cellulose diacylates having a D.S. of 2.2 to 2.6% such as cellulose disuccinate, cellulose dipalmitate, cellulose dioctanoate, cellulose dipenotate; co-esters of semipermeable celluloses such as cellulose acetate butyrate, cellulose acetate propionate; and the like.

Additional semipermeable polymers that can be used for manufacturing wall 12 comprise a member selected from the group consisting of acetaldehyde dimethyl cellulose acetate, cellulose acetate ethyl carbamate, cellulose acetate methyl carbamate, and cellulose dimethylamino acetate; semipermeable polyamides; semipermeable polyurethanes; semipermeable sulfonated polystyrenes; semipermeable cross-linked selectively permeable polymers formed by a coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); and semipermeable cross-linked poly(vinylbenzyltrimethyl ammonium chloride). The polymers are known to the art in U.S. Pat. Nos. 3,845,770; 3,916,899; 4,160,020; and 5,057,321; and in the *Handbook of Common Polymers*, by Scott, J. R. and Roff, W. J., 1971, published by CRC Press, Cleveland, Ohio. Semipermeable wall 12 comprises 35 wt % to 100 wt % of the semipermeable polymer for providing dosage form 10.

In another manufacture, wall 12 comprises additionally from 0 wt % to 65 wt %, and more preferably, 15 wt % to 50 wt % of a wall-forming member selected from the group consisting of a cellulose ether, hydroxypropylcellulose, hydroxypropylmethylcellulose, hydroxyethylcellulose, hydroxybutylcellulose, and polyethylene glycol. The total weight of all ingredients comprising wall 12 equals 100 wt %, wherein "wt %" denotes weight percent.

Internal compartment 14 comprises a first composition 15 and a second composition 16. First composition 15 comprises a drug 17, represented by dots, which drug 17 is present in first composition 15 in a therapeutically effective amount for producing an intended therapy. Generally, first composition 15 comprises 10 nanograms, ng, to 1200 milligrams, mg, of drug 17 for producing a therapeutic effect. First composition 15 comprises 15 wt % to 60 wt % of a hydrophilic polymer 18, represented by dashes, possessing a lower critical solution temperature. Generally, in one example operable for the purpose of the invention, the lower critical solution temperature comprising a hydrophilic polymer possesses a critical solution temperature of 35° C. to 50° C., however, other temperatures are within the scope of the invention. The phrase "lower critical solution temperature", as used for the purpose of this invention denotes the temperature at which the hydrophilic polymer 18 undergoes an in situ flocculation to provide a floc with drug 17 dispersed in the floc. The term "flocculation", as used herein means polymer 18 aggregates or precipitates in situ, in solution at the lower critical solution temperature. The term "floc" refers also to the flocculent mass formed as an aggregate or precipitate comprising drug 17 at the lower critical solution temperature.

First composition 15 comprises a dehydrating agent 19, represented by wavy lines. The dehydrating agent 19 possesses a greater affinity for water compared with lower critical solution temperature hydrophilic polymer 18. Representative of dehydrating agent 18 comprises a member selected from the group consisting of an electrolyte and a nonelectrolyte, that depress the lower critical solution temperature of polymer 18 to below body temperature of 32° C. by dehydrating polymer 18 and consequently enhancing polymer—polymer interaction and in situ flocculation. The depressing property of an electrolyte depends on the ability of its ions to hydrate in the presence of water, and the higher its affinity for water the higher depressing efficacy of the electrolyte. For example, cations and anions can be arranged in a lyotropic series of decreasing dehydrating ability as follows: $Mg^{++}>Ca^{++}>Sr^{++}>Ba^{++}>Li^+>Na^+>K^+>NH_4^+>Rb^+>Cs^+>Citrate^{3-}>SO_4^{2-}>Cl^->NO_3^->I^->CNS^-$, as reported in *Introduction to Colloid Surface Chemistry*, Third Edition, by D. J. Show, Butterworths, London, (1980). The affinity of a dehydrating agent for water can be ascertained by solubility parameter determinations as reported in *CRC Handbook of Chemistry and Physics*, 69th Edition, (1988–1989), published by CRC Press, Inc.; and in *Chemical Technician's Ready Reference Handbook*, Second Edition, pg 413–415, (1981), published by McGraw-Hill, Inc. The nonelectrolytes for depressing the lower critical solution temperature comprise polyhydroxy compound and a saccharide. Representative of polyhydroxy compounds comprise mannitol, sorbitol, maltitol, lactisol, maltotriitol, maltoletraitol, maltopentaitol, maltohexaitol, maltoheptaitol, 1,2,6-hexanetriol, pentaerythritol, 1,2,5 pentanetriol, and 1,2,4-butanetriol. The polyhydroxy compounds comprise diols, triols, tetraols, pentaneols, hexaneols, heptaneols, and octaneols. Representative saccharides comprise pentoses and hexoses, such as glucose, fructose, mannose, galactose, aldohexose, aldopentose, allose, altrose, talose, gulose, idose, and glucosone. Generally, first composition 15 comprises 10 wt % to 45 wt % of dehydrating agent 19, and in a presently preferred embodiment from 25 to 40 wt %.

First composition 15 comprises 0.1 wt % to 10 wt % of a surfactant 20 for assisting in providing an operable composition, which surfactants comprise propylene glycol alginate, propylene glycol agarose, propylene glycol ghatti, propylene glycol tragacanth, propylene glycol pectin, propylene glycol palmitate, propylene glycol oleate, propylene glycol stearate, propylene glycol lactate, propylene glycol maleate, propylene glycol malate, and propylene glycol tartrate; first composition 15 comprises 0.01 wt % to 22 wt % of a binder 21 comprising dextrin, polyvinylpyrrolidone, starch paste or gelatin; and, first composition comprises a manufacturing aid for reducing adhesiveness of the composition to the surface of dies and punches, wherein the lubricant comprises a member selected from the group consisting of aluminum stearate, stearic acid, calcium oleate, magnesium stearate, glyceryl behenate, potassium stearyl fumarate, and sodium stearyl fumarate.

Second composition 16, present in compartment 14, comprises a hydrophilic composition that comprises a hydrophilic polymer 23. The hydrophilic polymer exhibits the ability to swell and expand 2 to 60 fold in the presence of imbibed water and biological fluid, and thereby push first composition 15 from dosage form 10. The hydrophilic polymers retain a significant volume of water or biological fluid within the polymer structure. The hydrophilic polymers can be noncross-linked, or they can be lightly cross-linked. The cross-links can be covalent or ionic bonds with the polymer possessing the ability to swell in the presence of fluid, and when cross-linked, it will not dissolve in the fluid. The polymer can be of plant, animal or synthetic origin. Polymeric materials useful for the present purpose include poly(hydroxyalkyl methacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(-vinyl alcohol) having a low acetate residual; a water-swellable copolymer produced by a dispersion of finely divided copolymer of maleic anhydride with styrene, ethylene, propylene, or isobutylene; water swellable polymer of N-vinyl lactams; poly(vinyl alcohol) cross-linked with glyoxal, formaldehyde or glutaraldehyde; Cyanamer® polyacrylamide cross-linked with indene maleic anhydride; Carbopol® acidic carboxy polymer and its salt derivatives; polyacrylamides; water-swellable indene maleic anhydride polymers; Good-rite® polyacrylic acid having a molecular weight of 80,000 200,000; Polyox® polyethylene oxide polymers having a molecular weight of 100,000 to 7,000,000, and greater; starch graft copolymers; polyanions and polycations exchange polymers; starchpolyacrylonitrile copolymers. Aqua-Keep® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; copolymers of N-vinyl lactam with N-vinyl piperidione; Water-Lock® starch-graft poly(iodine acrylate-co-acrylamide); sodium carboxymethylcellulose; and the like.

Other hydrophilic polymers 23, in one preferred manufacture comprise hydrogels having a 15,000 to 7,500,000 molecular weight, including hydrogel polysaccharides. The hydrogel polysaccharides useful for making an expandable, push second composition comprise natural gums, seaweed extract, plant exudate, agar, agarose, algin, sodium alginate, potassium alginate, carrageenan, kappa-carrageenan, lambda-carrageenan, fucoidan, furcellaran, laminarin, hypnea, eucheuma, gum arabic, gum ghatti, gum karaya, gum tragacanth, guar gum, locust bean gum, quince psyllium, flax seed, okra gum, arabinogalactin, pectin, xanthan, scleroglucan, dextran, amylose, amylopectin, dextrin, acacia, karaya, guar, a swellable mixture of agar and carboxymethyl cellulose; a swellable composition comprising methyl cellulose mixed with a sparingly cross-linked agar; a blend of sodium alginate and locust bean gum; and the like. The hydrophilic polymers 23 comprising the hydrogels are known to the prior art in U.S. Pat. Nos. 3,865,108; 4,002,173; 4,169,066; 4,207,893; 4,211,681; 4,271,143; 4,277,366; 4,327,725; 4,449,983; and, 4,800,056; and in *Handbook of Common Polymers*, by Scott and Roff, published by the Chemical Rubber Company, Cleveland, Ohio. The amount of hydrophilic polymer 23 present in second composition comprises 20 wt % to 85 wt %.

Second composition 16 comprises an osmagent 24, also known as osmotically effective solute and osmotically effective compound that can be blended homogeneously or heterogeneously with the swellable polymer, to form a push member, are the osmotically effective solutes that are soluble in fluid imbibed into the swellable polymer, and exhibit an osmotic pressure gradient across the semipermeable wall against an exterior fluid. Osmotically effective osmagents useful for the present purpose include solid compounds selected from the group consisting of magnesium sulfate, magnesium chloride, sodium chloride, lithium chloride, potassium sulfate, sodium sulfate, mannitol, urea, sorbitol, inositol, sucrose, glucose and the like. The osmotic pressure in atmospheres, ATM, of the osmagents suitable for the invention with be greater than zero ATM, generally from zero ATM up to 500 ATM, or higher. The amount of osmagent blended with hydrophilic polymer 23 is 0 wt % to 65 wt %, and in one manufacture 7.5 wt % to 35 wt %.

The second composition 16 also comprises 0 to 4.5 wt %, preferably 0.01 wt % to 4.5 wt % of a lubricant 25 such as stearic acid and the like; 0 wt % to 1 wt % of a dye 26 such as D&C yellow No. 10, and/or 0 wt % to 1 wt % of a second dye such as FD&C Blue No. 1; and 2.5 wt % to 30 wt % of a binder 27 such as polyvinylpyrrolidone, starch, gelatin, dextrose, lactose, molasses, mucilage, waxes and polyethylene glycol.

Drawing FIG. 3 depicts dosage form 10 in operation in a biological environment of use. In drawing FIG. 3, hydrophilic polymer 23 is illustrated precipitated above its lower critical solution temperature, providing a floc with drug 17 dispersed in the floc. Accompanying drawing FIG. 4 depicts phase diagrams for different kinds of binary mixtures including one showing a lower critical solution temperature, as reported in *Molecular Thermodynamics of Fluid-Phase Equilibrium*, Second Edition, J. M. Prausnitz, R. N. Lichtenhalter, and Z. G. Azevido, published by Prentice-Hall, Inc., N.J., (1986). Drawing FIG. 4 pertains to the phase stability in four binary liquid mixtures. In drawing FIG. 4, 0 denotes an absence of a component 1, 1 denotes pure component 1, X denotes the fraction of component 1, and $T_c$ denotes the critical solution temperature.

Figure 5:
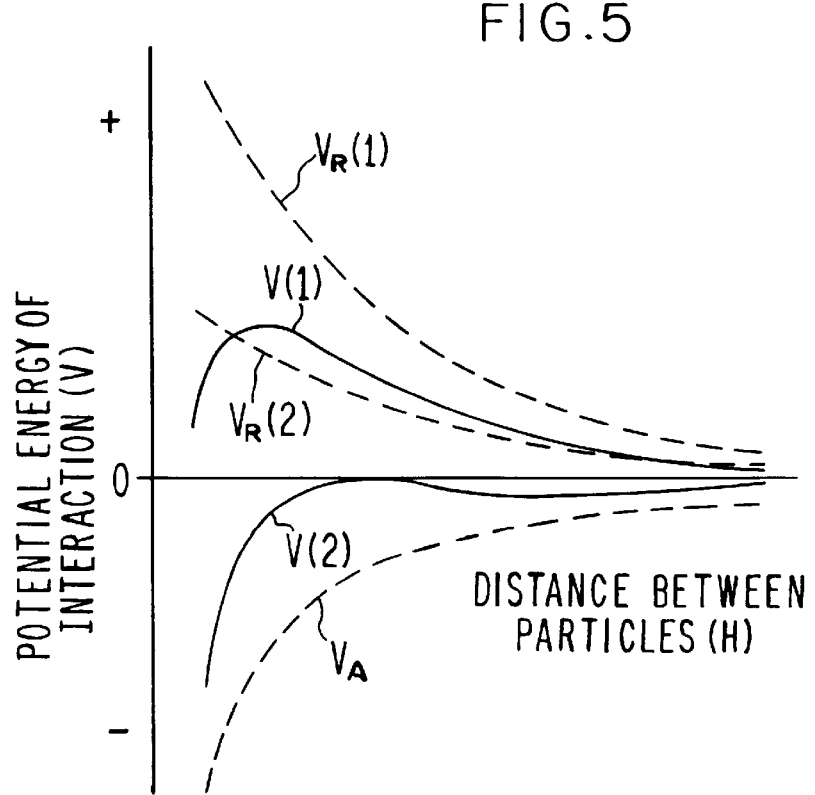
FIG. 5 depicts a series of total interaction energy curves embraced by the invention.

In operation, the total energy of interaction between the hydrophilic polymer dispersion is obtained from drawing FIG. 5, wherein is illustrated the total interaction energy curves (1) and (2), obtained by the summation of an attraction curve, $V_A$, with different repulsion curves, $V_{R(1)}$ and $V_{R(2)}$. The total potential curve V(1) shows a repulsive energy maximum, wherein the system should be stable, whereas in curve V(2), the double-layer repulsion does not predominate over Van der Waals attraction at an interparticle distance, hence the system should aggregate. Another characteristic of these potential energy curves is the presence of a secondary minimum at relatively large interparticle distance. When this minimum is moderately deep compared with KT (thermal energy), it gives rise to a loose, easily reversible flocculation. Generally, aggregation or coagulation refers to a primary minimum effect and flocculation refers to the secondary minimum or polymer bridging effect as seen in drawing FIG. 5. See *Introduction to Colloid and Surface Chemistry*, Third Edition, D. J. Shaw, published by Butterworths, London, (1980).

Figure 6:
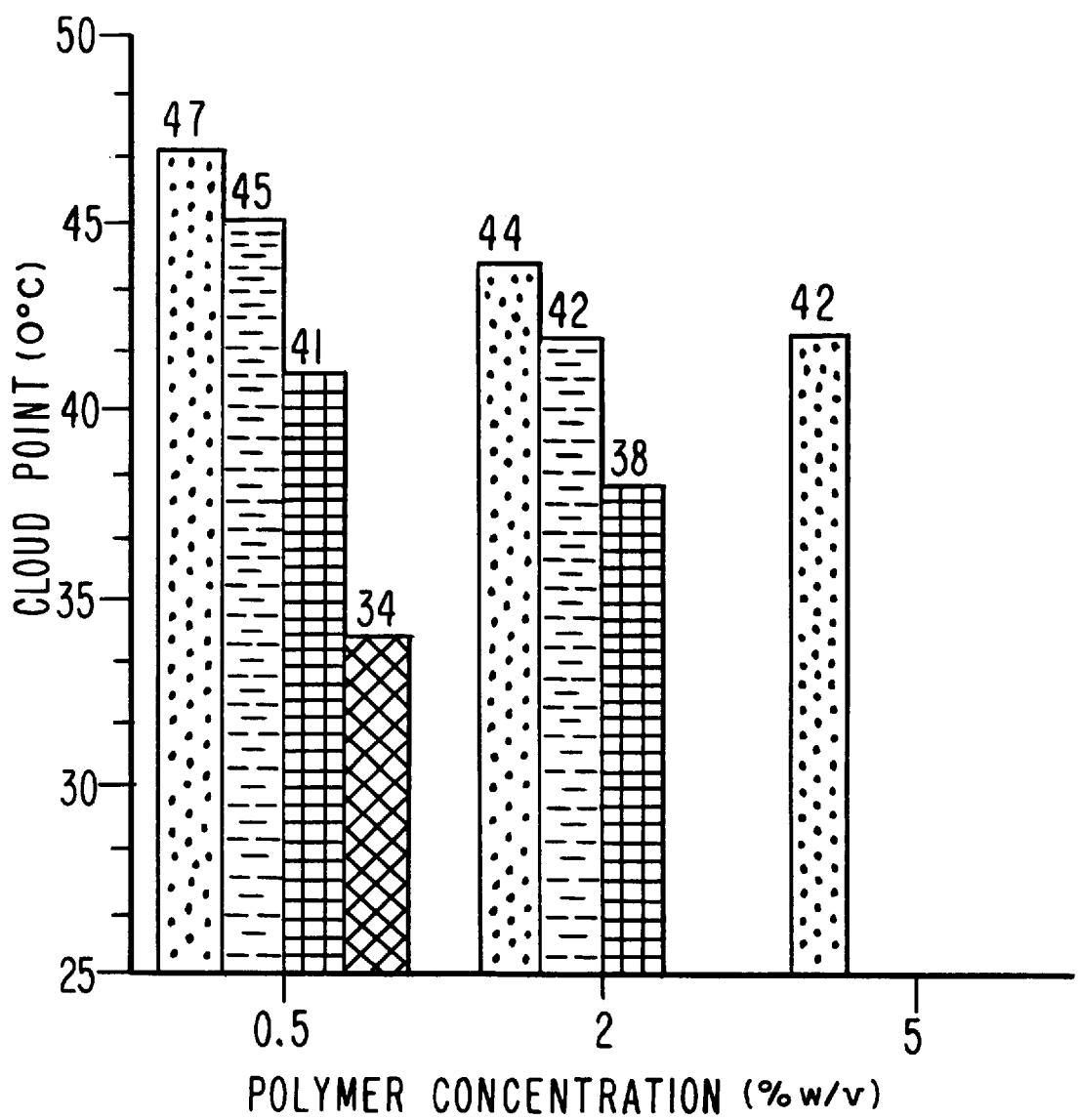
FIG. 6 depicts the cloud point of hydroxypropylcellulose solution as a function of the polymer and dehydrating mannitol concentrations.
Figure 7:
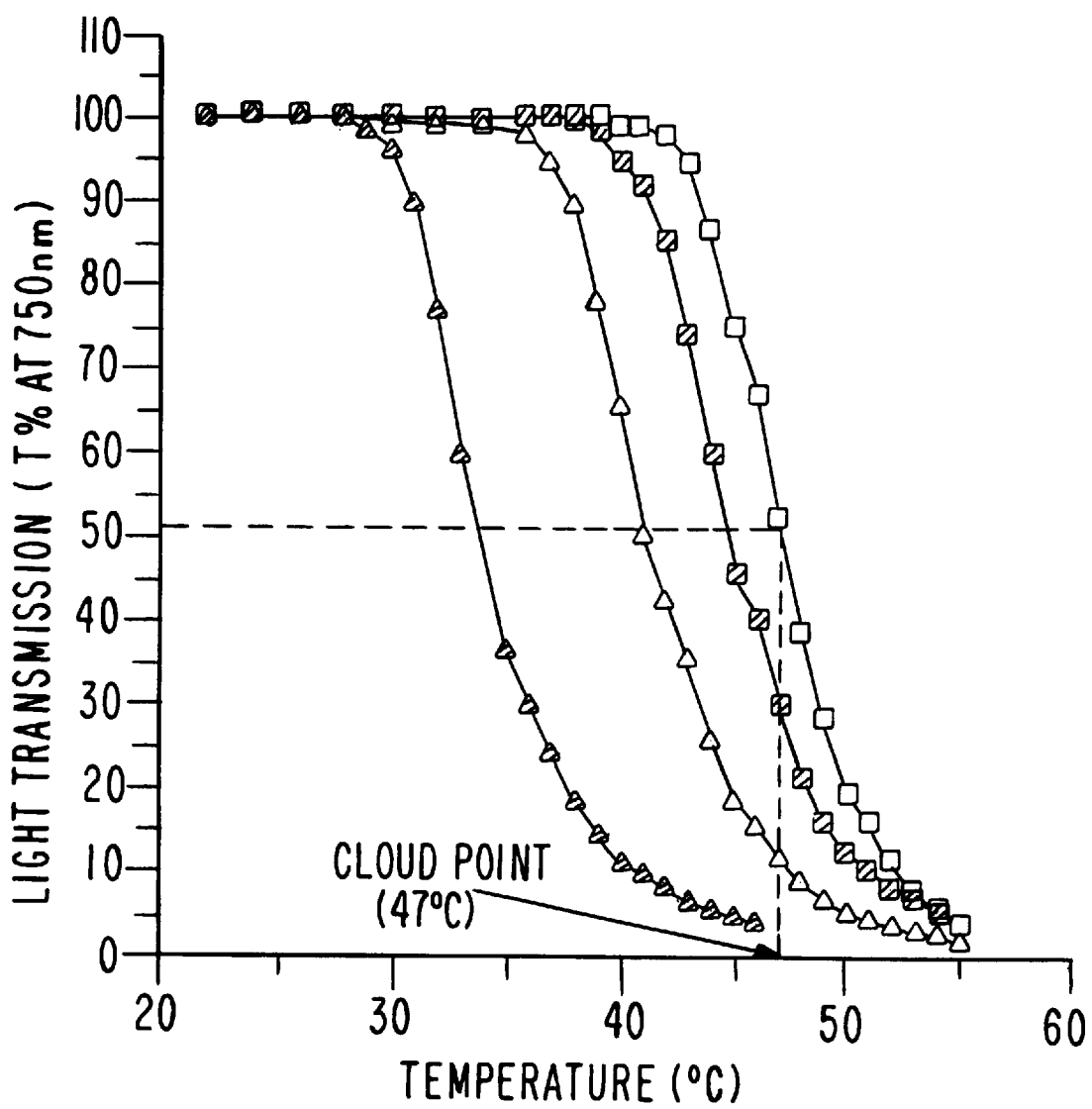
FIG. 7 depicts the effect of dehydrating mannitol concentration on the cloud point of hydroxypropylcellulose polymeric solutions; and, Drawing

The lower critical solution temperature for hydrophilic polymer 23 and for a corresponding hydrophilic polymeric gel 23 can be measured by procedures known to the prior art, such as with spectrophotometry, as reported by L. D. Taylor and L. D. Cerankowski, *J. Polym. Sci., Polym. Chem. Ed.*, Vol. 13, pg. 2551 (1975); M. M. Coleman, D. J. Skrovanek, and R. C. Painter, Applied Spetroscopy, Vol. 38, pp 448, (1984); and K. Mitchell, J. L. Ford, D. J. Armstrong, P. N. C. E. Elliot, C. Rostron an J. E. Hogan, *Intern. J. Pharm.*, Vol. 66, pg. 233, (1990), by differential scanning calorimetry as reported by L. C. Dong and A. S. Hoffman, *Proc. Intern. Sympmp. Control. Rel. Bioact. Mater.*, Vol. 17, pg 116, (1990) and I. Yamamoto, K. Iwaski, and S. Horotsu, *J. Phys. Soc. Jap.*, Vol. 58, pg. 210, (1989), and by nuclear magnetic resonance spectroscopy as reported by H. D. H. Stover and J. M. J. Frechet, *Macromolecules*, Vol. 22, pg. 1574 (1989). The spectrophotometrical method is used to measure the cloud point of the polymer exhibiting a lower critical solution temperature. "Cloud point" generally refers to the temperature where aqueous polymer becomes cloudy at the characteristic temperature with the cloudy suspension becoming clear at the same temperature, as discussed by F. M. Winnick, *Macromolecules*, Vol. 20, pg 2745, (1987); and by K. E. Min, J. S. Chiou, J. W. Barlow and D. R. Paul, *Polymer*, Vol. 28, pg. 1721, (1987). The spectrophotometrical method was used herein to study the lower critical solution temperature property of, for example, hydroxypropylcellulose solutions containing various amounts of mannitol and for other polymer dehydrating agent combinations. The procedure for this method for hydroxypropylcellulose and mannitol is as follows:

Hydroxypropylcellulose, in various amounts is dissolved in distilled water or in mannitol solutions comprising 64 mg per ml, 128 mg per ml, and 256 mg per ml, solubility at 37° C. as measured, to obtain hydroxypropylcellulose solutions with concentrations of 0.5, 2,0 and 5.0 mg per ml. Each hydroxypropylcellulose solution contained in a bottle, and was placed in a water bath, and circulated through a 1 cm flow cuvette. The water bath was equipped with a temperature regulator, and the temperature was increased gradually at a rate of 1° C./min. The temperature of solutions in the cuvette was monitored by a thermocouple, the lead of which was inserted into the cuvette through a tubing connecting the bottle and the cuvette. The light transmission, T%, of each solution was measured spectrophotometrically with a Perkin Elmer Lamda-3 UV spectrophotometer at a wavelength of 750 mm. Initially readings were taken at 2° C. intervals, which was reduced to 1° C. increments near the cloud point. The cloud point was ascertained as the temperature at which the light transmission was 50% of the transmission at room temperature. Accompanying drawing FIG. 6 depicts the cloud point of hydroxypropylcellulose solution as a function of the polymer and the mannitol concentrations. In drawing FIG. 6, the numbers above the bars indicate the cloud point for hydroxypropylcellulose. Further in drawing FIG. 6, the bar with dots represents a dehydrating mannitol concnetration expressed in mg/ml, or w/v, or zero; the bar with dashes represents a dehydrating mannitol concentration of 64 mg/ml; the bar with squares represents a dehydrating mannitol concentration of 128 mg/ml; and the bar with slanted lines depicts a dehydrating mannitol concentration of 256 mg/ml. Accompanying drawing FIG. 7 depicts the effects of mannitol concentrations on the cloud point of hydroxypropylcellulose solution, wherein the hydroxypropylcellulose concentration is 0.5% (w/v), weight/volume, for all solutions. In drawing FIG. 7, the mannitol concentration, (in mg/ml, w/v) is 0 for the clear square, 64 for the checkered square, 128 for a clear triangle, and 256 for a checkered triangle.

The flocculation of hydrophilic polymers 23 in saturated solutions of various dehydrating agents can be ascertained by a disintegration experiment. In the experiment, ¼ inch round tablets containing 300 mg of hydroxypropylcellulose and 1% magnesium stearate were prepared by direct compression with a laboratory Carver® press under 1 ton of compression force. The disintegration tests of these tablets were conducted in 100 ml of media at 37° C. The responses observed when the tablets were exposed to the solution containing the dehydrating agent comprise swelling to a sticky gel matrix; maintaining its integrity without noticeable change in appearance, or forming a white, intact and weak floc. At low dehydrating concentrations, the tablets hydrated to a sticky gel matrix as usually observed when an hydroxypropylcellulose tablet is exposed to water. At saturated concentrations of dehydrating sodium chloride, the tablets retain their integrity without any noticeable change in their appearance. At saturated concentrations of dehydrating mannitol, or dehydrating sorbitol, or dehydrating fructose, the tablets hydrated to white, intact flocs. The flocs disintegrated into a milky dispersion when experiencing vigorous shaking. The flocs appear as a sponge-like matrix, that comprises a porous, but continuous network, which compresses under pressure, leading to the continuous phase draining through channels in that network. Further experimental parameters are disclosed by M. M. Bobins, *ACS Symposium Series*, Vol. 448, pg 230, (1991), Eds.: El-Nokaly, D. Cornell, ACS, Washington, D.C.

Representative of hydrophilic polymers 23 operable for the mode and the manner of the invention comprise a member selected from the group consisting of alkylcellulose, hydroxyalkylcellulose, hydroxyalkylalkylcellulose, hydroxypropylcellulose, hydroxypropylmethylcellulose, hydroxyethylcellulose, poly (vinyl alcohol-vinyl acetate) copolymer, poly(ethylene glycol) monoether, polymethacrylic acid, long-chain quaternary salts, poly(n-vinyl-2-oxazolidine), poly(propylene glycol), partially formalized poly(vinyl alcohol), cyanoethylated-poly(vinyl alcohol), poly(N-isopropylacrylamide), poly(vinylmethylether), poly (ackylalkylacrylamide), poly(L-proline), poly(amino acid), poly(peptide) and proteins.

The expression "drug 17", as used for the purpose of the present invention, denotes aqueous hydrophilic drugs and aqueous hydrophobic drugs. The hydrophilicity and the hydrophobicity of a drug can be expressed as soluble and insoluble in an aqueous solution, a solvent, as disclosed in *Pharmaceutical Sciences*, by Remington, p 247 (1970) published by the Mack Publishing Company, Easton, Pa. The degree of solubility to insolubility of a drug is expressed in the accompanying table.

SOLUBILITY TABLE

| SOLUBILITY | PARTS OF AQUEOUS SOLVENT FOR 1 PART OF DRUG SOLUTE |
| --- | --- |
| Very soluble | Less than 1 |
| Freely soluble | From 1 to 10 |
| Soluble | From 10 to 30 |
| Sparingly soluble | From 30 to 100 |
| Slightly soluble | From 100 to 1000 |
| Very slightly soluble | From 1000 to 10,000 |
| Practically insoluble or Insoluble | More than 10,000 |

The solubility of a beneficial drug can be determined by known techniques. One method for ascertaining the solubility of an agent consists of preparing a saturated solution comprising the fluid plus the agent as ascertained by analyzing the amount of agent present in a definite quantity of the fluid. A simple apparatus for this purpose consists of a test tube of medium size fastened upright in a water bath maintained at a constant temperature and pressure, in which the fluid and agent are placed and stirred by a rotating glass spiral. After a given period of stirring, a weight of the fluid is analyzed and the stirring continued an additional period of time. If the analysis shows no increase of dissolve agent after successive periods of stirring, in the presence of excess solid agent in the fluid, the solution is saturated and the results are taken as the solubility of the product in the fluid. If the agent is soluble, an added osmotically effective compound optionally may not be needed: if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin*, No. 67 of the Hygienic Laboratory; *Encyclopedia of Science and Technology*, Vol. 12, pp 542–556, (1971) published by McGraw-Hill, Inc.; and *Encyclopaedic Dictionary of Physics*, Vol. 6, pp 547–557, (1962) published by Pergamon Press, Inc.

Dosage form 10 comprises a drug 17 that comprises any physiologically or pharmacologically active substance that produces a local or systemic effect in animals, including warm-blooded mammals, humans and primates; avians, household, sport and farm animals; laboratory animals; fishes; reptiles; and zoo animals. The term, "physiologically", as used herein, denotes the administration of drug 17 to produce generally normal levels and functions in a warm-blooded animal. The term, "pharmacologically" generally denotes variations in response to the amount of drug administered to the host. See *Stedman's Medical Dictionary*, (1966) published by Williams and Wilkins, Baltimore, Md.

The beneficial drug 17 that can be delivered by the dosage form includes inorganic and organic compounds without limitation, including drugs that act on the peripheral nerve, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, organ systems, reproductive system, skeletal system, autacoid systems, alimentary and excretory systems, inhibitors of autacoids, and histamine systems. The therapeutic drug 17 that can be delivered for acting on these recipients include anticonvulsants, analgesics, anti-Parkinsons, anti-inflammatories, anesthetics, antimicrobials, antimalarials, antiparasitic, antihypertensives, angiotensin converting enzyme inhibitor, antihistamines, antipyretics, alpha-adrenergic agonist, alpha-blockers, biocides, bactericides, bronchial dilators, beta-adrenergic stimulators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, ophthalmics, psychic energizers, fungicides, biocides, viricides, parasympathomimetics, sedatives, sympathomimetics, tranquilizers, urinary tract drugs, vaginal drugs, vitamins, calcium channel blockers, and the like.

Drug 17, that can be delivered by dosage form 10, is a drug that is very soluble in aqueous fluids, such as prochlorperazine edisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, methacholine chloride, pilocarpine hydrochloride, atropine sulfate, scopolamine bromide, isopropamide iodine, tridihexethyl chloride, phenformin hydrochloride, methylphenidate hydrochloride, cimetidine hydrochloride, theophylline cholinate, cephalexin hydrochloride, and the like.

Exemplary drugs that can be delivered by dosage form 10 and are slightly soluble in aqueous fluid comprise niplatin, ketoconazole, itraconazole, amphotericin, flucytosine, diphenidol, meclizine hydrochloride, clotrimazole, prochlorperazinemaleate, phenoxybenzamine, thiethylperazine maleate, anisindione, diphenadione, erythritol tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, estrogens, progestogens, corticosteroids, hydrocortisone, hydrocortisosterone acetate, cortisone acetate, triamcinolone, methyltesterone, 17-beta-estradiol, ethinyl estradiol, prazosin hydrochloride, ethinyl estradiol 3-methyl ether, prednisolone, 17-alpha-hydroxyprogesterone acetate, 19-norprogesterone, norgestrel, norethindrone, progesterone, norgesterone, morethynodrel, tixorortol pivalate, and the like.

Examples of other drugs 17 that can be delivered by dosage form 10 comprises aspirin, indomethacin, naproxen, fenoprofen, sulindac, indoprofen, nitroglycerin, propranolol, timolol, atenolol, alprenolol, cimetidine, clonidine, imipramine, levodopa, carbidopa, chlorpromazine, methyldopa, dihydroxyphenylalanine, levodopacarbidopa, pivaloyloxyethyl ester of alpha methyldopa, theophylline, calcium gluconate, ketoprofen, ibuprofen, cephalexin, erythromycin, hodperidol, beclomethasone, zomepirac, ferrous lactate, vincamine, diazepam, captopril, phenoxybenzamine, betamethasone, nifedipine, diltiazem, verapamil, milrinone, mandol, guanabenz, nystatin, cetylopyridinium chloride, chlorhexidine, latoronazole, clotrimazole, bifonazole, tolnaftate, hydrochlorothiazide, and the like. The beneficial drugs are known to the art in *Pharmaceutical Sciences*, 14th Ed., edited by Remington, (1979) published by Mack Publishing Co., Easton, Pa.; *The Drug, The Nurse, The Patient, Including Current Drug Handbook*, by Falconer et al., (1974–1976) published by Sunder Co., Philadelphia, Pa.; *Medicinal Chemistry*, 3rd Ed., Vol. 1 and 2, by Burger, published by Wiley- Interscience, NY and in *Physicians' Desk Reference*, 43rd Ed., (1989) published by Medical Economics Co., Oradell, N.J.

Drug 17 in dosage form 10 can be in various forms, such as uncharged molecules, molecular complexes, pharmacologically acceptable salts, such as hydrochloride, hydrobromide sulfate, laurate, palmitate, phosphate, nitrite, borate, acetate, maleate, tartrate, oleate, and salicylate. For acidic drugs, salts of metals, amines or organic cations; for example, quaternary ammonium can be used. Derivatives of drugs such as ester, ethers and amides can be used. Also, a drug that is water insoluble can be used in a form that is a water soluble derivative thereof to serve as a solute, and on its release from the device is converted by enzymes, hydrolyzed by body pH or other metabolic processes to the original biologically active form.

The dosage form 10 of this invention can be manufactured for delivering drug 17 to different biological receptor sites. Dosage form 10 can embrace a wide variety of shpaes, sizes and forms for delivering different drugs 17 to the indicated environment of use. For example, the dosage forms include buccal, implant, anal, rectal, artificial gland, cervical, intrauterine, ear, nose, subcutaneous, sublingual, and oral. The dosage form can be used for administering a drug to a patient at home, in hospitals, clinics, nursing homes, farms, sickrooms, and the like.

The expression, "exit means," as used herein, comprises means and methods suitable for the controlled metered release of drug 17 from compartment 14 of dosage form 10. The exit means comprises at least one passageway, or the like, through wall 12 for communicating with compartment 14. The expressions, "at least one passageway," comprises aperture, orifice, bore, pore, porous element, hollow fiber, capillary tube, porous overlay, porous insert, and the like. The expression also comprises a material that erodes or is leached from the wall in a fluid environment of use to produce at least one passageway in the wall. Representative materials suitable for forming at least one passageway, or a multiplicity of passageways, comprise erodible polymers such as polyglycolic acid or a polylactic acid member in the wall, a gelatinous filament, polyvinyl alcohol, leachable materials, such as fluid removable pore-forming polysaccharides, salts, oxides or the like. A plurality of passageways can be formed by leaching a material such as sorbitol, lactose, or the like from the wall. The passageway can have any shape, such as round, triangular, square, elliptical, slit, and the like. Dosage form 10 can be constructed with one or more passageways in spaced apart relations, or more than one passageway in spaced apart relations, or more than one passageway on a single surface of dosage form 10. Passageways and equipment for forming passageways are disclosed in Theeuwes et al, U.S. Pat. No. 3,845,770, issued November, 1974; Theeuwes et al, U.S. Pat. No. 3,916,899, issued November, 1975; Saunders et al, U.S. Pat. No. 4,063,064, issued December, 1977; and Theeuwes et al, U.S. Pat. No. 4,088,864, issued May, 1978. Passageways in osmotic systems formed by leaching, to provide controlled-release bores, are disclosed in Ayer et al, U.S. Pat. No. 4,200,098, issued April 1980; Ayer et al, U.S. Pat. No. 4,285,987, issued August, 1981; Theeuwes, U.S. Pat. No. 4,309,996, issued January, 1982; and Theeuwes, U.S. Pat. No. 4,320,759, issued March, 1982.

DESCRIPTION OF PROCESSES FOR PROVIDING THE INVENTION

Wall 12 of osmotic dosage form 10 can be formed in one technique using the air suspension procedure. This procedure consists in suspending and tumbling the compressed first and second composition in a current of air and wall forming composition until a wall is applied to the drug forming compartment. The air suspensions procedure is well-suited for independently forming the wall. The air suspension procedure is described in U.S. Pat. No. 2,799,241; *J. Pharm. Assoc.*, Vol. 48, pages 451 to 459, (1959); and ibid, Vol. 49, pages 82 to 84, (1960). Dosage form 10 can also be coated with a wall-forming composition in a Wurster® air suspension coater, using acetone-water cosolvent, 90:10, wt:wt, using 2.5 to 4 wt % solids. The Aeromatic® air suspension coater using a methylene dichloride methanol cosolvent, 87:13, v:v, also can be used for applying the wall. Other wall forming techniques such as pan coating can be used for providing dosage form 10. In the pan coating system, wall forming compositions are deposited by successive spraying of the composition on the bilayered compartment, accompanying by tumbling in a rotating pan. A pan coater is used to produce thicker walls. A larger volume of methanol can be used in a cosolvent to produce a thinner wall. Finally, the wall coated compartments are dried in a forced air oven at 30° C. to 50° C. for up to a week to free the dosage form of solvent. Generally, the walls formed by these techniques have a thickness of 2 to 20 mils with a presently preferred thickness of 4 to 10 mils.

Dosage form 10 of the invention is manufactured by standard manufacturing techniques. For example, in one manufacture, beneficial drug 10 and other ingredients comprising the first layer facing the exit means are blended and pressed into a solid layer. The drug and other ingredients can be blended also with a solvent and mixed into a solid or semisolid formed by conventional methods, such as ball-milling, calendering, stirring or rollmilling, and then pressed into a preselected shape. The first and second layers possess dimensions that correspond to the internal dimensions of the area the layer is to occupy in the dosage form and its also possesses dimensions corresponding to the second layer for forming a contacting arrangement therewith. Next, the osmopolymer or hydrogel second layer is placed in contact with the drug first layer. The layering of the drug layer and the osmopolymer layer can be fabricated by conventional press-layering techniques. Finally, the two layered compartment forming members that represent the first and second compositions are surrounded and coated with an outer wall. A passageway is laser drilled through the wall to contact the drug layer, with the dosage form optically oriented automatically by the laser equipment for forming the passageway on the preselected surface.

In another manufacture, the dosage form is manufactured by the wet granulation technique. In the wet granulation technique, drug 17 and the ingredients comprising the first layer are blended, using an organic or inorganic solvent, such as isopropyl alcohol-methylene dichloride 80/20 v/v as the granulation fluid. Other granulating fluid, such as water or denatured alcohol 100%, can be used for this purpose. The ingredients forming the first layer are individually passed through a 40 mesh screen and then thoroughly blended in a mixer. Next, other ingredients comprising the first layer are dissolved in a portion of the granulation fluid, such as the cosolvent described above. Then, the latter prepared wet blend in slowly added to the drug blend with continual mixing in the blender. The granulating fluid is added until a wet blend is produced, which wet mass then is forced through a 20 mesh screen onto oven trays. The blend is dried for 12 to 24 hours at 30° C. to 50° C. The dry granules are sized then with a 20 mesh screen. Next, a lubricant is passed through an 80 mesh screen and added to the dry screened granule blend. The granulation is put into milling jars and mixed on a jar mill for 10 to 15 minutes. The composition is pressed into layers, for example, in a Manesty® press layer press. The second layer is pressed in a similar manner.

Another manufacturing process that can be used for providing the compartment-forming composition comprises blending the powdered ingredients in a fluid bed granulator. After the powdered ingredients are dry blended in the granulator, a granulating fluid, for example poly(vinylpyrrolidone) in water, is sprayed onto the powders. The coated powders are then dried in a granulator. This process granulates all the ingredients present therein while adding the granulating fluid. After the granules are dried, a lubricant, such as stearic acid or magnesium stearate is blended, as above, into the mixture. The granules are pressed then in the manner described above.

The osmotic device of this invention is manufactured in another embodiment, by mixing a drug with composition forming ingredients and pressing the composition into a solid lamina possessing dimensions that correspond to the internal dimensions of the compartment space adjacent to a passageway. In another embodiment, the drug and other first composition forming ingredients and a solvent are mixed into a solid, or a semi-solid, by conventional methods, such as ballmilling, calendering, stirring or rollmilling, and then pressed into a preselected lamina forming shape. Next, a lamina of a composition comprising an osmopolymer and an optional osmagent are placed in contact with the lamina comprising the drug, and the two lamina comprising the laminate are surrounded with a semipermeable wall. The lamination of the first drug composition and the second osmopolymer optional osmagent composition can be accomplished by using a conventional two-layer tablet press technique. The wall can be applied by molding, spraying or dipping the pressed shapes with wall forming materials. Another and presently preferred technique that can be used for applying the wall is the air suspension coating procedure. This procedure consists in suspending the tumbling of the two layered laminate in current of air, until the wall forming composition surrounds the laminate. The air suspension procedure is described in U.S. Pat. No. 2,799,241; *J. Am. Pharm. Assoc.*, Vol. 48, pp 451–459 (1979); and, ibid, Vol. 49, pp 82–84 (1960). Other standard manufacturing procedures are described in *Modern Plastics Encyclopedia*, Vol. 46, pp 62–70 (1969); and in *Pharmaceutical Science*, by Remington, 14th Ed., pp 1626–1979, (1970), published by Mack Publishing Co., Easton, Pa.

Exemplary solvents suitable for manufacturing the wall, the laminates and laminae, include inert inorganic and organic solvents that do not adversely harm the materials and the final wall of the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethylacetate, methylene dichloride, ethylene dichloride, propylene dichloride, carbon tetrachloride, chloroform, nitrethane, nitropropane, tetrachloroethane, ethyl ether, isopropyl ether, cyclohexane, cyclooctane, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE EXAMPLES OF THE INVENTION

The following examples are merely illustrative of the present invention and they should not be considered as limiting the scope of the invention in ay way, as these examples and other equivalents thereof will become apparent to those versed in the art in the light of the present disclosure, the drawings and the accompanying claims.

EXAMPLE 1

A dosage form 10, designed, shaped and adapted for dispensing the beneficial drug nystatin to the oral cavity is manufactured as follows: first, a first composition or drug-layer composition, is prepared, comprising in weight percent, 18.33 wt % of nystatin, 30.00 wt % of hydroxypropylcellulose, having an 80,000 average molecular weight, 28.00 wt % mannitol, 4.67 wt % propylene glycol alginate, 7.50 wt % polyvinylpyrrolidone, 6 wt % cherry flavor, and 2 wt % orange flavor, are each passed through a 40-mesh stainless steel screen and then blended in a Glatt® fluid-bed granulator and sprayed with an additional 2.50 wt % aqueous polyvinylpyrrolidone until homogeneous granules form. These granules are passed through a 16-mesh stainless steel screen and then mixed with 1.00 wt % stearic acid.

Next, the second composition, the osmotic push layer composition, is prepared comprising, in weight percent, 55 wt % kappa-carrageenan, 28.0 wt % sorbitol, 7.5 wt % polyvinylpyrrolidone, 0.7 wt % D+C yellow # 10, and 0.3 wt % FD+C blue #1 are each passed through a 40-mesh stainless steel screen and then blended in a Glatt® fluid-bed granulator, and sprayed with additional 7.5% polyvinylpyrrolidone in purified water, until homogeneous granules form. These granules are passed through a 16-mesh stainless steel screen and mixed with 1.0 wt % stearic acid.

Next, the drug-layer and the push-layer granules are compressed into a bilaminate tablet arrangement. First, 240 mg of the drug-layer granules are added to a ⅝ inch caplet punch and tamped, then 160 mg of the push-layer granules are added to the punch and the two laminae are pressed with a Kilian® Tablet Press under a force of about 2 tons into a contacting laminated arrangement.

Next, bilaminate arrangements are coated with a semipermeable wall. The wall-forming composition comprises, in weight percent, 70 wt % cellulose acetate having an acetyl content of 39.8%, and 30 wt % polyethylene glycol having a 3,350 molecular weight. The wall forming composition is dissolved in acetone/water, (90/10, wt/wt) mixed cosolvent to make a 4% solid solution. The wall-forming composition is sprayed onto the bilaminated arrangement in a Freund Hi-Coater®. The wall weight per the arrangement is about 24.4 mg. Finally, a 20 mil exit orifice is drilled mechanically on the drug-layer side of the dosage form. The residual solvent is removed by drying the dosage form at 30° C. and ambient humidity for 3 days. The final manufactured dosage form delivers the drug nystatin at an average rate of 15.0 mg/hr, with 85% of the nystatin delivered in 2.9 hours, as depicted in drawing FIG. 8.

EXAMPLE 2

The procedure of Example 1 is repeated in this example for providing the dosage form. In this example, the dosage form is comprised of the first composition, or drug-layer, and the second composition, or osmotic-push layer, with both identical to those provided in Example 1, respectively. In this example, the wall composition weighed 28.1 mg and it comprises 40% cellulose acetate having an acetyl content of 39.8% and 60% polyethylene glycol having a molecular weight of 3,350. The high flux of the semipermeable wall results in the dosage form delivering the nystatin at an average controlled rate of 28.6 mg/hr, with 85% of the drug released in 1.5 hours, as depicted in drawing FIG. 9.

EXAMPLE 3

The procedure of Example 1 is repeated in this example for providing a dosage form wherein the manufacturing and structural components are as disclosed, except that the wall comprised 50% cellulose acetate having an acetyl content of 39.8% and 50% polyethylene glycol having a molecular weight of 3,350. The dosage form delivers at an average dosage-form controlled rate of 25.9 mg/hr, with 85% of drug released in 1.6 hours, as depicted in drawing FIG. 10.

EXAMPLE 4

Figure 11:
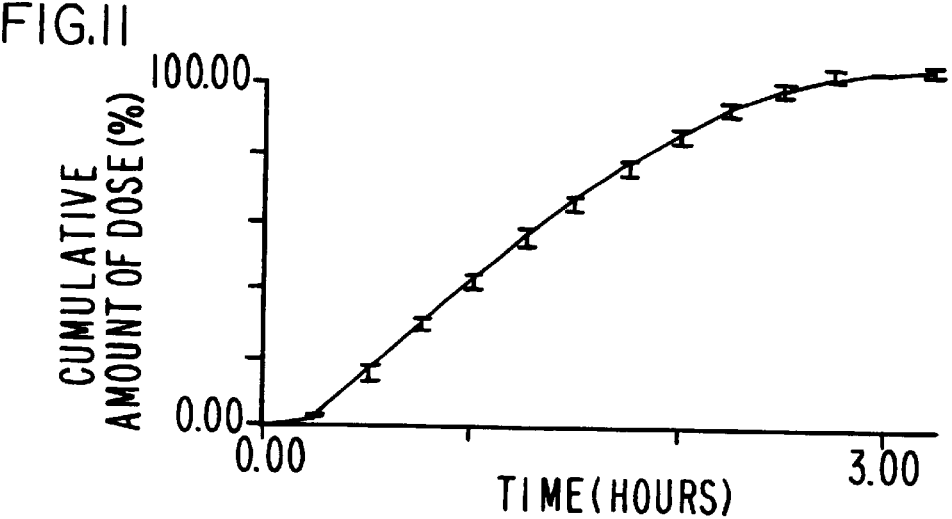

The procedure of Example 1 is repeated in this example, with all procedures, as described previously. In this example, the semipermeable wall weighed 35.6 mg and the semipermeable wall comprised 60% cellulose acetate comprising an acetyl content of 39.8% and 40% polyethylene glycol having a molecular weight of 3,350. The dosage form delivers the drug nystatin at an average dosage controlled rate of 19.6 mg/hr, with 85% of the drug released in 2.0 hours, as depicted in drawing FIG. 11. The dosage form is designed, shaped and adapted for administering the drug in the buccal cavity of a patient in need of therapy.

EXAMPLE 5

Figure 12:
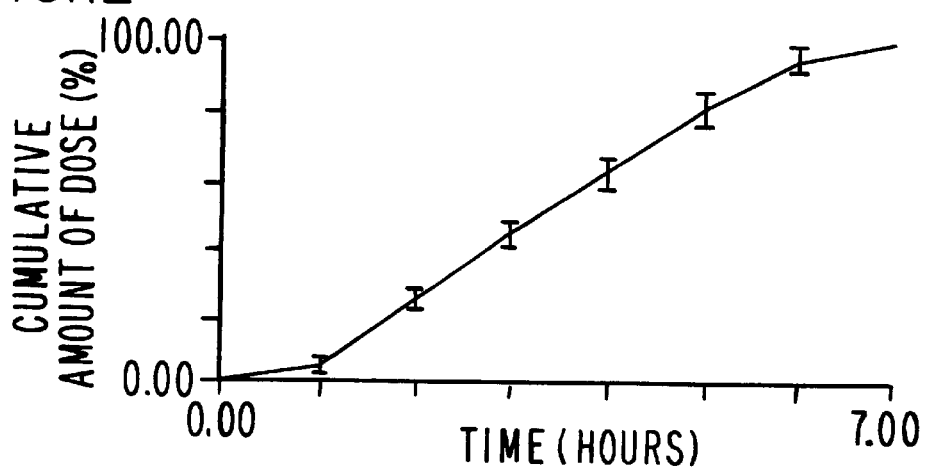

A buccal dosage form is provided by following the procedure of Example 1, with all the conditions as previously set forth, except that in this example, the semipermeable wall weighed 34.4 mg and comprised 80% cellulose acetate and 20% polyethylene glycol having a molecular weight of 3,350. The dosage form delivers nystatin at a controlled rate of 7.1 mg/hr, with 85% of the nystatin delivered in 5.3 hours as depicted in drawing FIG. 12.

EXAMPLE 6

Figure 13:
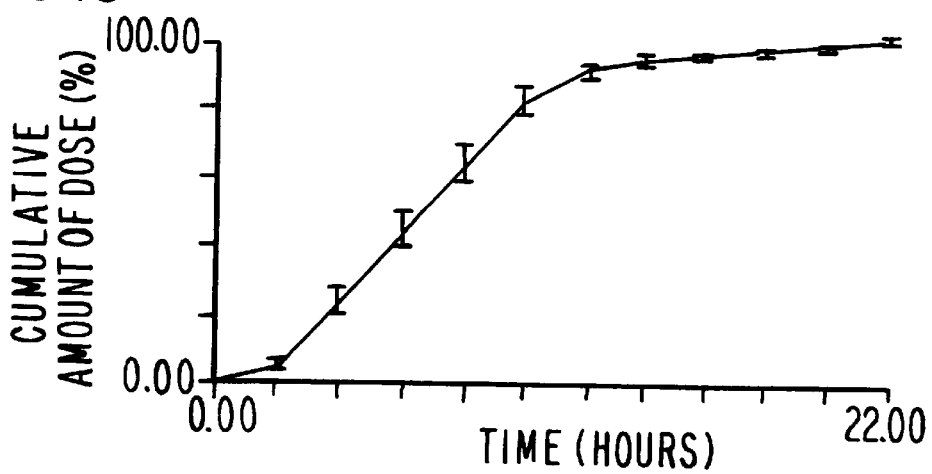

The procedure of Example 1 is repeated in this example with all the conditions as previously set forth. The dosage form provided by this example comprised a semipermeable wall weighing 27.0 mg, which wall comprises 90% cellulose having an acetyl content of 39.8% and 10% polyethylene glycol having a molecular weight of 3,350. The dosage form delivers nystatin at an average rate of 3.6 mg/hr with 85% of the nystatin delivered in 10.7 hours as depicted by drawing FIG. 13.

EXAMPLE 7

Figure 14:
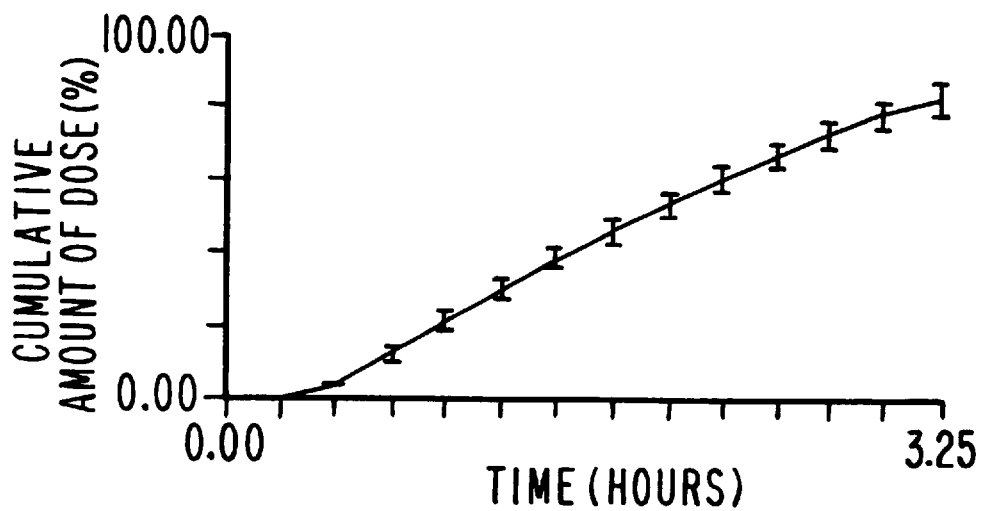

A mucosal osmotic therapeutic system for the controlled delivery of the beneficial drug nystatin in the oral cavity of a patient in need of nystatin therapy is manufactured according to the above procedure. The therapeutic system of this example comprises a first composition weighing 240 mg, comprising 18.0% nystatin, 30% hydroxypropylcellulose, 23% mannitol, 10% hydroxypropyl glycol alginate, 10% polyvinylpyrrolidone, 7% chocolate flavor, 1% mint flavor and 1% stearic acid. The therapeutic system comprises a second composition weighing 160 mg comprising 68% kappa-carrageenan, 15% sorbitol, 15% polyvinylpyrrolidone, 0.7% D+C yellow #10, 0.3% FD+C blue #1, and 1% stearic acid. The therapeutic system comprises a semipermeable wall, weighing 50.9 mg, which semipermeable wall comprises 60% cellulose acetate having an acetyl content of 39.8% and 40% polyethylene glycol having a molecular weight of 3,350. The therapeutic system delivers the drug nystatin at a controlled rate of 12.7 mg/hr with 85% of the nystatin delivered in 3.4 hours, as depicted in drawing FIG. 14. In this example, a chocolate/mint combination is used instead of a cherry/orange combination in the drug composition, to mask the bitter taste of nystatin, thereby enhancing the acceptance of the therapeutic system for buccal and/or sublingual therapy.

EXAMPLE 8

Figure 15:
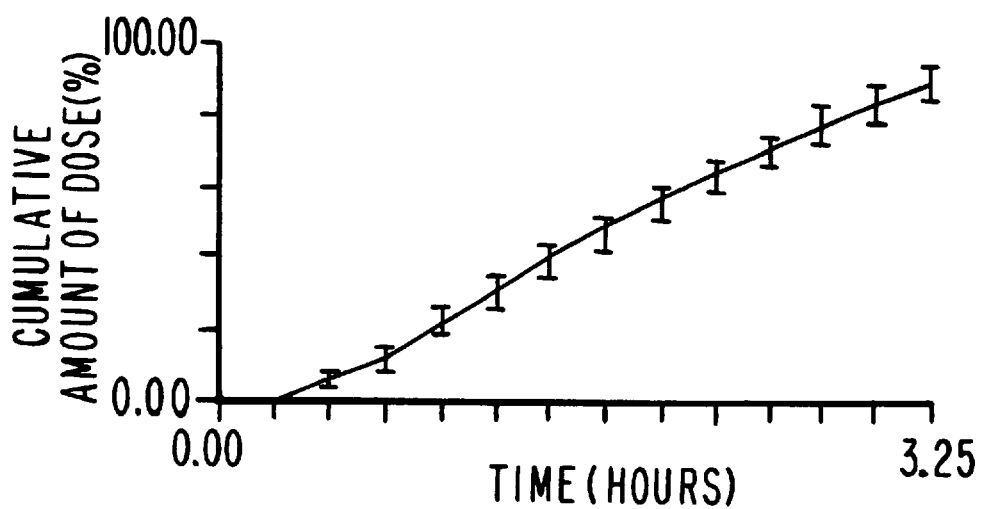

A delivery system prepared according to this example, comprises a drug composition as described in Example 7. In this example, the osmotic-push composition comprises 68% sodium alginate, 15% calcium sulfate, 15% polyvinylpyrrolidone, 0.7% D+C yellow #10, 0.3% FD+C blue #1 and 1% stearic acid, and a wall composition comprising 60% cellulose acetate having an acetyl content 39.8% and 40% polyethylene glycol having a molecular weight of 3,350. The delivery system administers nystatin at a controlled rate of 13.2 mg/hr, with 85% of the drug delivered in 3.1 hours as disclosed in drawing FIG. 15. The present example demonstrate the use of a sodium alginate/calcium sulfate combination for pushing the drug composition from the delivery system.

EXAMPLE 9

Following the procedure of the above examples, a dosage form is shaped and designed for administering a drug in the gastrointestinal tract, wherein the dosage form is manufactured wherein the first composition comprises a drug selected from the group consisting of bromocriptine; bromocriptine and its therapeutically acceptable salts; bromocriptine mesylate; ergot derivatives including lisuride, pergolide, and mesulergine; levodopa; carbidopa; levodopa-carbidopa; amantadine; deprenyl; trihexyphenidyl; benztropine; biperiden; ethopropazine; procyclidine; dopamine agonists; monamine oxidase inhibitors, anti-chlolinergics including benztropine mesylate, trihexyphenidyl hydrochloride, procyclidine hydrochloride, biperident hydrochloride, and ethopropazine.

EXAMPLE 10

The procedure of the above examples is followed herein, with all conditions as previously set forth, except that the drug in the present example comprises a member selected from the group consisting of fludrocortisone, fludrocortisone acetate, hydrocortisone, beclomethasone, beclomethasone dipropionate, betamethasone, betamethasone benzoate, betamethasone dipropionate, betamethasone sodium phosphate, betamethasone acetate, betamethasone valerate, cortisone acetate, dexamethasone, and dexamethasone acetate.

EXAMPLE 11

The procedure of the above examples is followed with all the conditions as previously set forth, except that in this example, the drug is a member selected from the group consisting of monensin, amphotericin B, flucytosine, ketoconazole, miconazole, itraconazole, triacetin, fluconazole, griseofulvin, clotrimazole, econazole, terconazole, butoconazole, oxiconazole, sulconazole, ciclopirox olamine, cisonazole, tolnaftate, naftifine, bifonazole, cilofungin, flucytosine, natamycin, and polyene antifungal antibiotic.

DISCLOSURE OF METHODS OF USING THE INVENTION

The present invention provides many methods for delivering a drug to a patient in need of therapy. One method pertains to a method for delivering a beneficial drug into the oral cavity of a patient. This method concerns administering a drug buccally for both its topical and systemic therapy. In this method, the drug can pass into an through the highly vascularized buccal tissues of the mouth for effective therapy. Buccal administration is needed for treating diseases of the mouth that require constant therapy. For example, one such disease condition is candidiasis of the oral cavity. A recent study has shown that about 94% of patients having acquired immunodeficiency syndrome, and 72% of the patients with acquired immunodeficiency syndrome related complex diseases exhibit a fungal infection in the oral cavity, see Barr & Marder, *AIDS: A Guide for Dental Practice*, pp 53–62, (1987).

Prior to this invention, the treatment of oral candidiasis consists of dosing anti-fungal drugs into the mouth, pharynx and oesophagus. Unfortunately, when anti-fungal drugs are administered by gargling or with rinses, the anti-fungal drugs are cleared from the mouth in a matter of minutes. The present invention overcomes the prior art shortcomings for treating oral diseases, by providing a unique dosage form that is able to continuously deliver therapeutically effective doses of a drug, into the oral cavity for extended periods of time, generally from greater than zero time up to four hours, or longer.

One method for providing oral therapy comprises the steps of: (A) admitting orally into the warm-blooded animal, such as a patient, a dosage form comprising: (1) a wall that surrounds a compartment, the wall comprising a semipermeable composition, permeable to the passage of fluid; (2) a first composition in the compartment comprising a hydrophilic polymer comprising a lower critical solution temperature, a dosage amount of a drug, and a dehydrating agent that exhibits an affinity for aqueous solutions; (3) a second composition in the compartment comprising an expandable composition for imbibing and absorbing fluid for pushing and displacing the first composition from the dosage form; (4) at least one exit in the wall for releasing the first composition from the dosage form; (B) imbibing fluid through the semipermeable wall into the first composition causing the hydrophilic polymer to flocculate above its lower critical solution temperature in the presence of the dehydrating agent to form a floc comprising the drug; (C) imbibing fluid into the second composition, causing the second composition to expand and push against the first composition; and thereby (D) delivering the drug from the dosage form through the exit into the oral cavity of the warm-blooded animal to produce the intended therapeutic effect over the desired period of time.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the systems illustrated and described can be made without departing from the spirit of the invention.

We claim:

1. A dosage form for administering a drug to a patient, wherein the dosage form comprises:

(1) a wall comprising a semipermeable composition, which wall defines a compartment;

(2) 10 ng to 1200 mg of drug in the compartment;

(3) a push composition in the compartment for pushing the drug from the dosage form;

(4) at least one exit port in the dosage form for delivering the drug from the dosage form; and wherein the dosage form is characterized by the compartment comprising:

(5) 15 wt % to 60 wt % of a hydrophilic polymer that precipitates in situ in the presence of fluid that enters the compartment and means for causing the hydrophilic polymer to precipitate comprising the drug whereby the dosage form, administers the drug to the patient.

\* \* \* \* \*